United States Patent
Jarowski (12)

(10) Patent No.: US 6,602,909 B1
(45) Date of Patent: Aug. 5, 2003

(54) SELECTED ESSENTIAL AMINO ACID SUPPLEMENTATION OF DIETARY PROTEINS TO LOWER URINARY UREA AND PEAK GLUCOSE LEVELS

(76) Inventor: Charles Ignatius Jarowski, 67 Harbor La., Massapequa Park, NY (US) 11762

( * ) Notice: Subject to any disclaimer, the term of this patent is extended or adjusted under 35 U.S.C. 154(b) by 0 days.

(21) Appl. No.: 10/053,265

(22) Filed: Jan. 23, 2002

(51) Int. Cl.⁷ .............................................. A61K 31/198
(52) U.S. Cl. ...................................... 514/561; 514/562
(58) Field of Search ................................ 514/561, 562; 426/656

(56) References Cited

U.S. PATENT DOCUMENTS 3,080,234 A    3/1963    Jarowski ..................... 424/11
5,559,142 A  *  9/1996    Jaworski ..................... 514/419

OTHER PUBLICATIONS

Serougne et al., Annals of Nutrition and Metabolism, 27(5) 386–95 (1983).*

* cited by examiner

*Primary Examiner*—Phyllis G. Spivack

(57) ABSTRACT

Depending upon the quantity of protein being consumed, one or two unit doses of a blend of L-Tryptophan (80 mgs), L-Methionine (90 mgs), L-Valine (103 mgs) and L-Lysine (102 mgs as the hydrochloride salt) used as a supplement will lower urinary urea excretion and post prandial blood glucose levels.

1 Claim, No Drawings

SELECTED ESSENTIAL AMINO ACID SUPPLEMENTATION OF DIETARY PROTEINS TO LOWER URINARY UREA AND PEAK GLUCOSE LEVELS

Depending upon the quantity of protein being consumed, one or more unit doses of a blend of L-Tryptophan (80 mgs), L-Methionine (90 mgs), L-Valine (103 mgs) and L-Lysine monohydrochloride (128 mgs) was calculated to be a universal dietary supplement for 61 commonly used foods (C. I. Jarowski, U.S. Pat. No. 5,559,142). The levels of supplementation were derived by taking into account the average human fasting plasma concentrations of the eight essential amino acids plus L-Tyrosine and L-Cystine. The latter two non-essential amino acids were included since they are L-Phenylalanine-sparing and L-Methionine-sparing respectively.

Earlier studies in Sprague-Dawley rats demonstrated that essential amino acid supplemented rations lowered serum urea levels 44% (G. M. Torre, V. D. Lynch and C. I. Jarowski, J. Pharm. Sci., 70, 114 (1981). The levels of L-Tryptophan, L-Lysine and L-Threonine used to supplement the commercial rat ration were derived by taking into account the average fasting plasma concentrations of the essential amino acids of Sprague-Dawley rats.

A replicated human study demonstrated that when two unit doses of the quartette of essential amino acids mentioned above were taken immediately after each meal 24-hour urinary urea was reduced 25 to 28%. The unit doses were administered in #0 hard gelatin capsules. Typical meals used are shown in Table I.

TABLE I. RECOVERY OF URINARY UREA OVER A TWENTY FOUR HOUR PERIOD AFTER CONSUMPTION OF IDENTICAL MEALS WITH AND WITHOUT ESSENTIAL AMINO ACID SUPPLEMENTATION

Protocol: Breakfast was consumed from 7:30 to 8:00 AM. Lunch was eaten from 12:00 Noon to 12:30 P.M. Dinner was consumed from 6:00 to 6:30 PM. The supplemented meals were taken three days after the unsupplemented ones. The supplement taken after each meal consisted of two #0 hard gelatin capsules, each capsule contained 80 mgs of L-Tryptophan, 90 mgs of Methionine, 103 mgs of L-Valine and 128 mgs of L-Lysine monohydrochloride. Pooled samples of urine were collected for 24 hours.

Breakfast: One-half cup of rice (6.9 grams of protein), 2 cups of water, one chicken egg (12.8 gms of protein), one-half cup of Cow's Milk (4.03 grams of protein), one half of a banana, a cup of coffee, 10 ml of evaporated milk (0.7 gram of protein), a glass of orange juice, 10 Ritz crackers (10 grams of wheat protein), one teaspoon of Psyllium Hydrocolloid and one Multivitamin/Multimineral tablet. Total protein: 34.43 grams.

Lunch: Three slices of Turkey Breast (3 grams of protein), two pieces of potato bread (4 grams of protein), piece of Swiss cheese (5 grams of protein), cup of coffee, 10 ml of evaporated Cow's Milk (0.7 gram of protein). Total protein: 12.7 grams.

Dinner: Swanson's Hungry Man Turkey Dinner (30 grams of protein), cup of coffee, 10 ml of evaporated Cow's Milk (0.7 gram of protein), 8 Ritz crackers (8 grams of protein). Total protein: 38.7 grams.

Results: Without supplement 11.56 grams of urinary urea were collected. With 2 units of supplement taken immediately after each meal, 8.34 grams of urea were collected, a drop of 28% compared with the unsupplemented meals.

Post-prandial glucose levels following consumption of prepared meals such as meat, vegetables and salad or sandwiches with lettuce and tomatoes did not exhibit significant elevations above the fasting range. However cooked cereals such as rice or wheat yielded surprisingly elevated post-prandial glucose levels. The use of the quartette of essential amino acids as supplements effectively lowered the peak blood glucose levels. Typical results are shown in Table II.

TABLE II. LOWERING PEAK POST-PRANDIAL BLOOD GLUCOSE LEVELS BY SELECTED ESSENTIAL AMINO ACID SUPPLEMENTATION

Protocol: Fasting blood glucose levels were determined with the use of the Accu-Chek blood glucose meter. The Glucowatch developed by Cygnus, Inc. was also used. The Standard Breakfast used consisted of: 46 grams of Instant Rice (3 grams of protein), 61.64 grams of Egg Albumin (AllWhites, 6.7 grams of protein), one half cup of Cow's Milk (1% Fat, 3.15 grams of protein), one quarter teaspoon of salt, one cup of water, one cup of coffee, one gram of non-dairy creamer.

| Test | Fasting Blood Glucose Level | Completion of Breakfast | Blood Glucose Measurements | Supplement |
|---|---|---|---|---|
| 1 | 100 mg % | 7:30 AM | 7:45 AM: 290 mg %; 8:53 AM: 186 mg %; 10:30 AM: 99 mg % | None |
| 2 | 100 mg % | 7:55 AM | 8:20 AM: 155 mg %; 8:40 AM: 154 mg %; 8:55 AM: 157 mg %; 9:11 AM: 157 mg %; 9:26 AM: 140 mg %; 9:59 AM: 101 mg % | 1 Unit before Breakfast |
| 3 | 90 mg % | 9:02 AM | 9:16 AM: 148 mg %; 9:45 AM: 144 mg %; 10:32 AM: 122 mg %; 11:02 AM: 106 mg % | 2 Units before Breakfast |
| 4. | 100 mg % | 7:31 AM | 7:29 AM: 130 mg %; 7:49 AM: 214 mg %; 8:28 AM: 209 mg %; 8:48 AM: 280 mg %; 9:29 AM: 118 mg %; 9:49 AM: 78 mg % 10:09 AM: 62 mg %; 10:32 AM: 62 mg % | None Used the Glucowatch |

Note
The Accu-Chek meter was used for Tests 1, 2 and 3,

What is claimed is:
1. A method for lowering peak post-prandial blood glucose levels and lowering urinary urea by supplementing dietary proteins with a encapsulated blend of 80 mgs L-Tryptophan, 90 mgs of L-Methionine, 103 mgs of L-Valine and 102 mgs of L-Lysine as the hydrochloride salt.

* * * * *